United States Patent
Garcia et al.

(10) Patent No.: US 10,639,099 B2
(45) Date of Patent: May 5, 2020

(54) CATHETER HAVING A DISTAL SECTION WITH SPRING SECTIONS FOR BIASED DEFLECTION

(75) Inventors: Ariel Garcia, Glendora, CA (US); Jeffrey W. Schultz, Chino, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 98 days.

(21) Appl. No.: 13/481,691

(22) Filed: May 25, 2012

(65) Prior Publication Data
US 2013/0317375 A1 Nov. 28, 2013

(51) Int. Cl.
*A61B 18/14* (2006.01)
*A61M 25/01* (2006.01)
*A61B 18/00* (2006.01)
*A61M 25/00* (2006.01)
*A61B 34/20* (2016.01)

(52) U.S. Cl.
CPC ..... *A61B 18/1492* (2013.01); *A61M 25/0138* (2013.01); *A61B 34/20* (2016.02); *A61B 2018/00011* (2013.01); *A61B 2018/00029* (2013.01); *A61B 2018/00083* (2013.01); *A61B 2018/00107* (2013.01); *A61B 2018/00821* (2013.01); *A61B 2018/00839* (2013.01); *A61B 2218/002* (2013.01); *A61M 25/0051* (2013.01); *A61M 2025/0161* (2013.01); *A61M 2025/0166* (2013.01)

(58) Field of Classification Search
CPC .......... A61B 1/0051; A61B 1/005; A61B 2017/00305; A61B 17/3431; A61B 17/7026; A61B 17/7028; A61B 17/7029; A61B 17/7031; A61B 18/1492; A61B 18/22; A61B 2019/343; A61B 1/008; A61B 2018/1467; A61B 2017/00309; A61C 1/18; A61M 25/0138; A61M 25/0051
USPC .......................................... 606/46; 604/95.04
See application file for complete search history.

(56) References Cited

U.S. PATENT DOCUMENTS

| | | | |
|---|---|---|---|
| 3,109,461 A | 11/1963 | Wolff et al. |
| 3,757,768 A | 9/1973 | Kline |
| 4,353,358 A | 10/1982 | Emerson |
| 4,742,817 A | 5/1988 | Kawashima et al. |

(Continued)

FOREIGN PATENT DOCUMENTS

| | | |
|---|---|---|
| CN | 101766502 A | 7/2010 |
| CN | 102232869 A | 11/2011 |

(Continued)

OTHER PUBLICATIONS

European Search Report dated Jul. 5, 2004 for related European Application No. 04251137.8, 3 pages.

(Continued)

*Primary Examiner* — Jaymi Della
(74) *Attorney, Agent, or Firm* — Etan S. Chatlynne; Robert Calderon Safran & Cole P.C.

(57) ABSTRACT

A catheter has a distal section that includes a spring member having at least a slot, a rib and a spine for biasing the distal section for deflection within a single plane. Depending on the plurality and orientation of slot(s), rib(s) and spine(s)s, the distal section can allow for deflection in two opposing directions while allowing only limited deflection in perpendicular directions to maintain torquability, axial loading capabilities, and side force performance.

13 Claims, 12 Drawing Sheets

(56) References Cited

U.S. PATENT DOCUMENTS

| | | |
|---|---|---|
| 4,753,223 A | 6/1988 | Bremer |
| 4,911,148 A | 3/1990 | Sosnowski et al. |
| 5,228,441 A * | 7/1993 | Lundquist .......... A61B 18/1492 600/380 |
| 5,273,535 A | 12/1993 | Edwards et al. |
| RE34,502 E | 1/1994 | Webster, Jr. |
| 5,281,217 A | 1/1994 | Edwards et al. |
| 5,304,131 A | 4/1994 | Paskar |
| 5,315,996 A | 5/1994 | Lundquist |
| 5,322,064 A * | 6/1994 | Lundquist ................. 600/381 |
| 5,381,782 A * | 1/1995 | DeLaRama .......... A61B 1/0056 138/118 |
| 5,383,852 A | 1/1995 | Stevens-Wright |
| 5,391,147 A | 2/1995 | Imran et al. |
| 5,391,199 A | 2/1995 | Ben-Haim |
| 5,437,288 A | 8/1995 | Schwartz et al. |
| 5,467,763 A | 11/1995 | McMahon et al. |
| 5,477,856 A * | 12/1995 | Lundquist .......... A61B 18/1492 600/373 |
| 5,517,989 A | 5/1996 | Frisbie et al. |
| 5,843,152 A | 12/1998 | Tu et al. |
| 5,849,011 A | 12/1998 | Jones et al. |
| 5,891,088 A | 4/1999 | Thompson et al. |
| 5,897,529 A | 4/1999 | Ponzi |
| 5,911,720 A | 6/1999 | Bourne et al. |
| 5,919,199 A | 7/1999 | Mers Kelly et al. |
| 5,935,102 A | 8/1999 | Bowden et al. |
| 5,961,513 A | 10/1999 | Swanson et al. |
| 5,964,757 A | 10/1999 | Ponzi |
| 5,971,975 A | 10/1999 | Mills et al. |
| 6,012,494 A | 1/2000 | Balazs |
| 6,027,863 A | 2/2000 | Donadio, III |
| 6,048,339 A | 4/2000 | Zirps et al. |
| 6,102,886 A | 8/2000 | Lundquist et al. |
| 6,119,041 A | 9/2000 | Pomeranz et al. |
| 6,123,699 A | 9/2000 | Webster, Jr. |
| 6,146,381 A | 11/2000 | Bowe et al. |
| 6,152,911 A | 11/2000 | Giannoble |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,409 B1 | 4/2001 | Ellman et al. |
| 6,254,588 B1 | 7/2001 | Jones et al. |
| 6,292,695 B1 | 9/2001 | Webster, Jr. et al. |
| 6,332,881 B1 | 12/2001 | Carner et al. |
| 6,338,725 B1 | 1/2002 | Hermann et al. |
| 6,371,955 B1 | 4/2002 | Fuimaono et al. |
| 6,428,489 B1 * | 8/2002 | Jacobsen .......... A61M 25/0054 600/585 |
| 6,458,123 B1 * | 10/2002 | Brucker et al. ................. 606/41 |
| 6,485,455 B1 | 11/2002 | Thompson et al. |
| 6,491,626 B1 | 12/2002 | Stone et al. |
| 6,522,930 B1 | 2/2003 | Schaer et al. |
| 6,533,770 B1 | 3/2003 | Lepulu et al. |
| 6,585,717 B1 | 7/2003 | Wittenberger et al. |
| 6,585,718 B2 | 7/2003 | Hayzelden et al. |
| 6,591,472 B1 | 7/2003 | Noone et al. |
| 6,628,976 B1 | 9/2003 | Fuimaono et al. |
| 6,647,281 B2 | 11/2003 | Morency |
| 6,690,963 B2 | 2/2004 | Ben-Haim et al. |
| 6,699,241 B2 | 3/2004 | Rappaport et al. |
| 6,733,499 B2 | 5/2004 | Scheib |
| 6,795,721 B2 | 9/2004 | Coleman et al. |
| 6,817,999 B2 | 11/2004 | Berube et al. |
| 6,866,662 B2 | 3/2005 | Fuimaono et al. |
| 6,893,436 B2 | 5/2005 | Woodard et al. |
| 6,913,604 B2 | 7/2005 | Mihalik et al. |
| 7,008,375 B2 | 3/2006 | Weisel |
| 7,099,717 B2 | 8/2006 | Woodard et al. |
| 7,435,240 B2 | 10/2008 | Barkhahn et al. |
| 8,348,888 B2 | 1/2013 | Selkee |
| 2002/0120253 A1 | 8/2002 | Ouchi |
| 2002/0165461 A1 * | 11/2002 | Hayzelden et al. .......... 600/523 |
| 2003/0009208 A1 | 1/2003 | Snyder et al. |
| 2003/0105453 A1 | 6/2003 | Stewart et al. |
| 2004/0181136 A1 * | 9/2004 | McDaniel .......... A61M 25/0138 600/374 |
| 2004/0199051 A1 | 10/2004 | Weisel |
| 2005/0273085 A1 * | 12/2005 | Hinman .............. A61B 1/0055 606/1 |
| 2006/0189896 A1 * | 8/2006 | Davis ................ A61M 25/0013 600/585 |
| 2007/0066878 A1 * | 3/2007 | Worley .............. A61B 18/1492 600/374 |
| 2007/0208252 A1 * | 9/2007 | Makower ...................... 600/424 |
| 2008/0127704 A1 | 6/2008 | Yamanaka et al. |
| 2008/0211728 A1 | 9/2008 | Eray |
| 2008/0255540 A1 | 10/2008 | Selkee |
| 2008/0300462 A1 * | 12/2008 | Intoccia ............. A61B 1/00071 600/146 |
| 2009/0018497 A1 | 1/2009 | Birchard et al. |
| 2009/0036833 A1 * | 2/2009 | Parins ................... A61M 25/00 604/164.13 |
| 2009/0141683 A1 | 6/2009 | Grinshpun et al. |
| 2009/0171187 A1 | 7/2009 | Gerhart et al. |
| 2009/0306653 A1 | 12/2009 | Anderson |
| 2009/0312756 A1 * | 12/2009 | Schlesinger et al. ........... 606/41 |
| 2010/0069834 A1 | 3/2010 | Schultz |
| 2010/0152731 A1 | 6/2010 | de la Rama et al. |
| 2010/0168548 A1 | 7/2010 | Govari et al. |
| 2010/0168666 A1 | 7/2010 | Tegg |
| 2010/0168827 A1 | 7/2010 | Schultz |
| 2010/0222859 A1 | 9/2010 | Govari et al. |
| 2011/0004157 A1 * | 1/2011 | Dewaele ............ A61B 1/00071 604/95.01 |
| 2011/0102395 A1 | 5/2011 | Cheng et al. |
| 2011/0264089 A1 | 10/2011 | Zirkle et al. |
| 2012/0130173 A1 * | 5/2012 | Lutze ................. A61B 1/00071 600/146 |
| 2013/0006238 A1 | 1/2013 | Ditter et al. |
| 2013/0231657 A1 * | 9/2013 | Datta ................ A61M 25/0138 606/41 |
| 2013/0253505 A1 | 9/2013 | Schultz |
| 2013/0317375 A1 | 11/2013 | Garcia et al. |

FOREIGN PATENT DOCUMENTS

| | | |
|---|---|---|
| EP | 0 521 595 A2 | 1/1993 |
| EP | 0937481 A | 8/1999 |
| EP | 2 380 518 A2 | 10/2011 |
| JP | H07255855 A | 10/1995 |
| JP | 2004533892 A | 11/2004 |
| JP | 2011505747 A | 2/2011 |
| JP | 2011224373 A | 11/2011 |
| JP | 2011229920 A | 11/2011 |
| JP | 2012510831 A | 5/2012 |
| WO | WO 2010/063078 A1 | 6/2010 |
| WO | 2010148088 A2 | 12/2010 |
| WO | WO 2010136275 A1 * | 12/2010 |
| WO | WO 2012/019229 | 2/2012 |

OTHER PUBLICATIONS

Extended European Search Report dated Sep. 17, 2013 for EP application No. 13169246.9 (6 pages).

Extended European Search Report dated Jul. 16, 2013 in EP Application No. 13160787.1, 12 pages.

Australian Office Action issued in Application No. AU2013205935 dated Feb. 28, 2017, 4 pages.

Chinese Office Action issued in Application No. CN201310196351 dated Apr. 5, 2017, 12 pages.

Chinese Office Action issued in Application No. CN201310196351 dated Jun. 2, 2016, 9 pages.

Japanese Office Action issued in Application No. JP 2013-109703 dated Oct. 25, 2016, 4 pages.

JPO Notification of Reasons for Refusal dated in JP Patent Application No. JP2013-061576, dated Dec. 20, 2016 with English Language Translation, 11 pages.

* cited by examiner

CATHETER HAVING A DISTAL SECTION WITH SPRING SECTIONS FOR BIASED DEFLECTION

FIELD OF INVENTION

The present invention relates to an electrophysiologic catheter that is particularly useful for ablation and sensing electrical activity of heart tissue.

BACKGROUND OF INVENTION

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure—mapping followed by ablation—electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into a chamber of the heart. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

Heating of the tissue occurs due to its electrical resistivity. The tissue is heated sufficiently to cause cellular destruction in the cardiac tissue resulting in formation of a lesion within the cardiac tissue which is electrically non-conductive. During this process, heating of the ablation electrode also occurs as a result of conduction from the heated tissue to the electrode itself. If the electrode temperature becomes sufficiently high, possibly above 60° C., a thin transparent coating of dehydrated blood can form on the surface of the electrode. If the temperature continues to rise, this dehydrated layer of blood can become progressively thicker resulting in blood coagulation on the electrode surface. Because dehydrated biological material has a higher electrical resistance than tissue, impedance to the flow of electrical energy into the tissue also increases. If the impedance increases sufficiently, an impedance rise occurs and the catheter must be removed from the body and the tip electrode cleaned.

In a typical application of RF current, circulating blood provides some cooling of the ablation electrode. Another method is to irrigate the ablation electrode, e.g., with physiologic saline at room temperature, to actively cool the ablation electrode instead of relying on the more passive physiological cooling provided by the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the catheter. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into the patient and the increased clinical load required to monitor and possibly refill the injection devices during a procedure. In addition to irrigation flow during ablation, a maintenance flow, typically a lower flow rate, is required throughout the procedure to prevent backflow of blood into the coolant passages. Thus, reducing coolant flow by utilizing it as efficiently as possible is a desirable design objective.

Another consideration is the ability to control the exact position and orientation of the catheter tip. This is ability is critical and largely determines the usefulness of the catheter. It is generally known to incorporate into electrophysiology catheters an electromagnetic (EM) tri-axis location/position sensor for determining the location of a catheter's distal end. An EM sensor in the catheter, typically near the catheter's distal end within the distal tip, gives rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

U.S. Pat. No. 5,391,199, the entire disclosure of which is incorporated herein by reference, describes a position-responsive catheter comprising a miniature sensor coil contained in the catheter's distal end. The coil generates electrical signals in response to externally-applied magnetic fields, which are produced by field-generator coils placed outside the patient's body. The electrical signals are analyzed to determine three-dimensional coordinates of the coil.

U.S. Pat. No. 6,690,963, the entire disclosure of which is hereby incorporated by reference, is directed to a locating system for determining the location and orientation of an invasive medical instrument, for example a catheter or endoscope, relative to a reference frame, comprising: a plurality of field generators which generate known, distinguishable fields, preferably continuous AC magnetic fields, in response to drive signals; a plurality of sensors situated in the invasive medical instrument proximate the distal end thereof which generate sensor signals in response to said fields; and a signal processor which has an input for a plurality of signals corresponding to said drive signals and said sensor signals and which produces the three location coordinates and three orientation coordinates of a point on the invasive medical instrument.

Because of the size of the tip electrode and the limited interior space therein, the EM sensor is often positioned outside of the tip electrode, proximally thereof, and often off-axis from the tip electrode which can reduce the accuracy of the position sensing capabilities of the sensor. Being outside the tip electrode, the position sensor is also exposed to bending stresses and can limit the flexibility and deflection of the distal tip section. Moreover, the sensor can be damaged by RF energy during ablation.

Where the distal tip is irrigated, the efficiency of irrigated cooling becomes a significant factor as ablation procedures can last five or six hours resulting in extensive fluid-loading in the patient. Conventional irrigated tip electrodes typically operate with a flow rate of about 17 ml/minute at below about 30 watts of RF ablation energy to about 30-50 ml/minute at about 30 watts or greater.

Current catheters include irrigated ring electrodes that are adapted for ablation. Such catheters include coil or single axis sensors (SASs) for visualization of the irrigated ring electrodes. However, the sensors are typically housed in a dedicated lumen of a multi-lumened tubing typically used with deflectable catheters. As lumens are needed for other components, such as puller wires, lead wires, and/or irrigation tubing, it becomes difficult to maintain typical catheter sizes. As catheters become more complex, more components are incorporated and thus the allocation of space for each component becomes more challenging.

Deflectable catheters are known. A control handle typically provides an actuator by which a user can deflect the catheter uni-directionally (in one direction) or bi-directionally (in opposite directions within a plane). Linear ablation catheters are utilized to create one or more RF lesions at a given time by means of either uni-polar or bi-polar ablations. The size of the resulting lesion(s) is highly dependent upon good contact of the electrodes with the cardiac tissue. Current linear catheter designs place the ring electrodes on a deflectable or flexible portion. However, if the portion is too stiff, it does not conform to the tissue and the electrodes cannot make solid contact for effective lesions. If the region between the ring electrodes deflects too much during catheter deflection, the ring electrodes may be pulled away from the tissue also preventing the formation of effective lesions.

Accordingly, it is desirable that a catheter be adapted for mapping and ablation with improved cooling and position sensing characteristics by providing a tip section that carries irrigated tip and ring electrodes on a structure that is deflectable and contractible in a more controlled and predictable manner.

SUMMARY OF THE INVENTION

The present invention is directed to a catheter having a distal section with a spring member that allows for biased and more predictable deflection to enable better contact between tissue and electrodes carried on the distal section. The spring member has an elongated hollow structure on which ring electrodes are mounted at selected locations along the length of the structure. At least one section of the spring member extending between the ring electrodes has a predetermined cut pattern that includes at least one row of alternating slots and ribs along a first side of the structure and at least one longitudinal spine along a second side of the structure, where the first side is relatively more compressible and the second side is relatively less compressible, in providing the distal section with biased deflection within a plane defined by the two sides. Alternatively, where each section of the spring member has two rows of slots and ribs opposing each other along a first diameter and two longitudinal spines opposing each other along a second diameter, the distal section has a biased deflection in two opposing directions in a first plane defined by the first diameter while having limited, if any, deflection in a second plane defined by the second diameter. Where the first and second diameters are generally perpendicular, the spring member allows the distal section to have bi-directional deflection in the first plane while allowing limited, if any, deflection in the second plane to maintain torquability, axial loading capabilities, and side force performance.

Configured for irrigation, each ring electrode carried on the spring member is formed to provide a gap reservoir between the ring electrode and the spring member (and its cover). For each ring electrode, a support member is positioned in the lumen of the spring member under the ring electrode to support it and to enable delivery of irrigation fluid to the ring electrode. The support member is configured with multiple lumens for components extending through the distal section, one lumen of which receives an irrigation tubing that defines an irrigation path for fluid delivery to each ring electrode. A radial irrigation passage is formed in the support member and the spring member to provide fluid communication between the irrigation tubing and the gap reservoir of each ring electrode.

Carried on the support member for each ring electrode is a location sensor, e.g., a single axis coil sensor. The sensor is carried on an outer surface of the support member so that lumens within the support member can be used for other components such as lead wires, thermocouple wires, puller wires, irrigation fluid, and/or sensor cable which typically occupy less space than a location sensor.

The catheter includes a tip electrode having a shell wall that defines a cavity through which fluid flows and exits via fluid ports formed in the shell wall. The cavity is sealed by an internal member that extends into the cavity to safely house a position sensor for the tip electrode. A proximal portion of the internal member disperses fluid entering the tip electrode for a more uniform flow through the cavity. As such, fluid is fed to the more distal fluid ports in the tip electrode for more uniform cooling at all locations on the tip electrode.

BRIEF DESCRIPTION OF THE DRAWINGS

These and other features and advantages of the present invention will be better understood by reference to the following detailed description when considered in conjunction with the accompanying drawings wherein:

FIG. 7A is an end cross-sectional view of the tip electrode of FIG. 7, taken along line A-A.

FIG. 7B is an end cross-sectional view of the tip electrode of FIG. 7, taken along line B-B.

FIG. 7C is an end cross-sectional view of the tip electrode of FIG. 7, taken along line C-C.

DETAILED DESCRIPTION OF THE INVENTION

Figure 1:
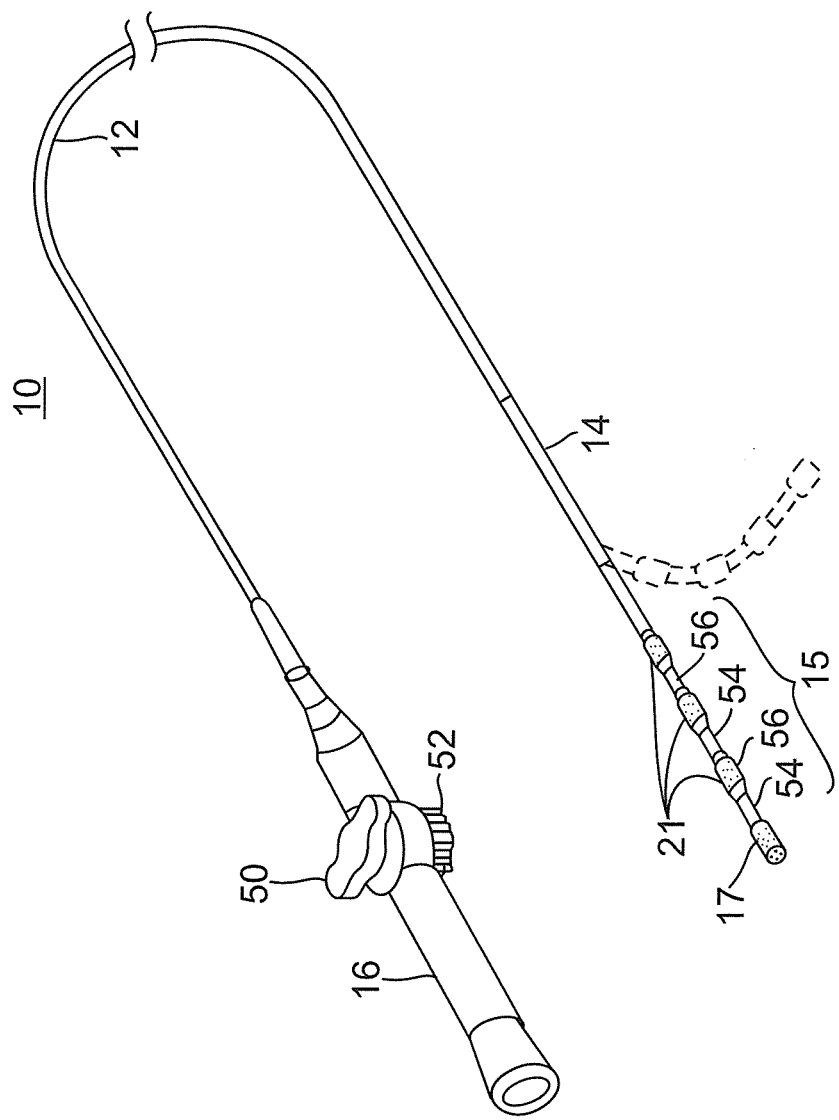
FIG. 1 is a perspective of a catheter according to an embodiment of the present invention.

FIG. 1 illustrates an embodiment of a catheter 10 carrying irrigated tip and ring electrodes with improved deflection characteristics. The catheter has an elongated catheter body 12 with proximal and distal ends, an intermediate deflectable section 14 at the distal end of the catheter body 12, and a distal section 15 which carries an irrigated tip electrode 17 and a plurality of irrigated ring electrodes 21. The catheter also includes a control handle 16 at the proximal end of the catheter body 12 for controlling deflection of at least the intermediate section 14. Advantageously, the distal section 15 has a spring member that enables a more controlled and biased deflection, including uni- or bi-directional deflection within a single plane. Along its length, the spring member houses discrete support members, each of which supports a respective ring electrode while allowing the spring member as a whole to deflect more predictably in enabling better contact between the tissue and the electrodes for forming more effective lesions.

Figure 2A:
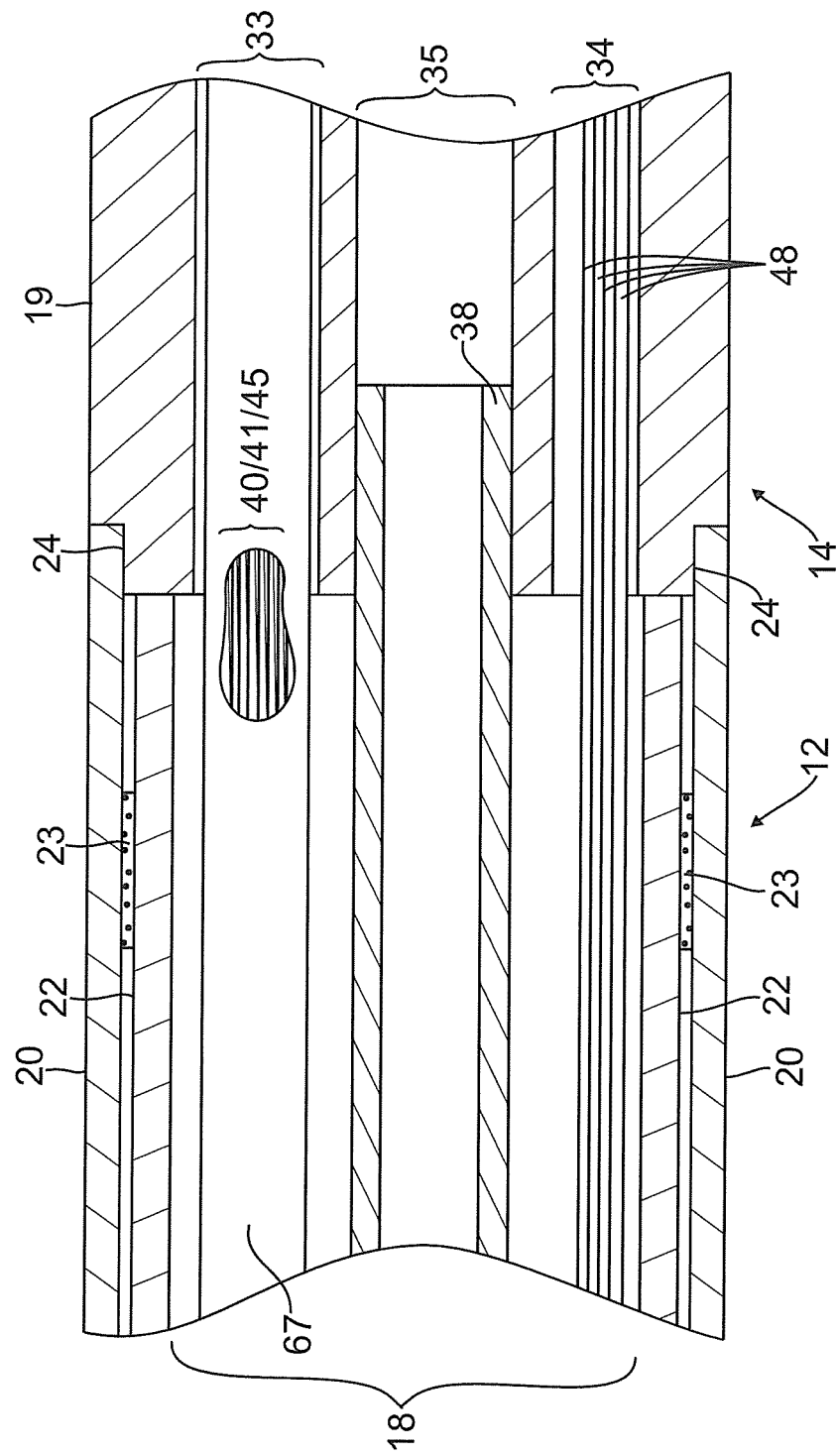
FIG. 2A is a side cross-sectional view of the catheter FIG. 1, showing a junction between a catheter body and a deflectable intermediate section, taken along a first diameter.
Figure 2B:
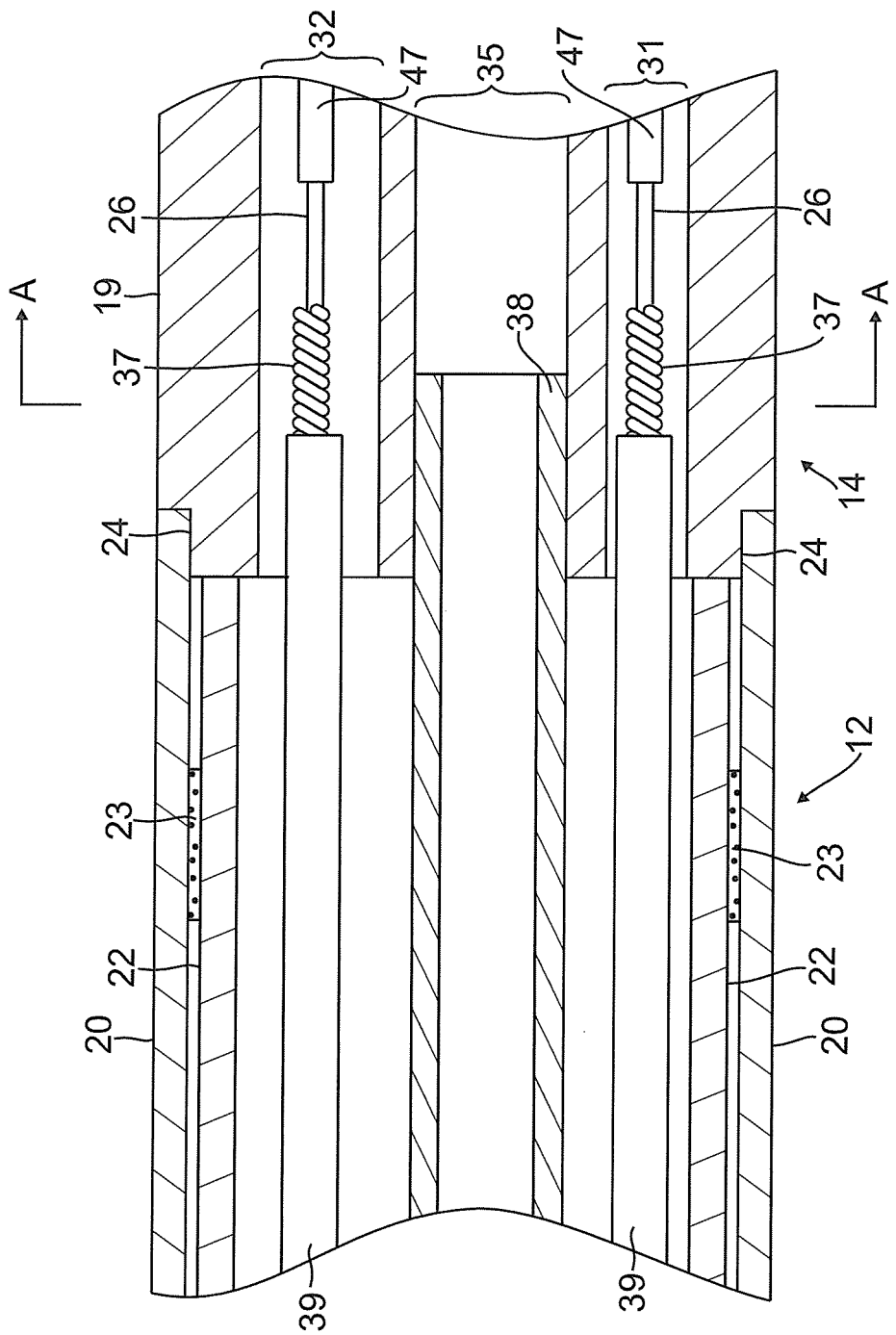
FIG. 2B is a side cross-sectional view of the catheter of FIG. 1, showing a junction between a catheter body and a deflectable intermediate section, taken a long a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint (not shown) is formed between proximal ends of the stiffening tube 20 and outer wall 22 using a slower drying but stronger glue, e.g., polyurethane.

Components that extend between the control handle 16 and at least the intermediate deflectable section 14 pass through the central lumen 18 of the catheter body 12. These components include lead wires 40 for the tip electrode 17 and ring electrodes 21 on the distal section 15, an irrigation tubing 38 for delivering fluid to the distal section 15, cables 48 for position/location sensors 36R and 36T located in the tip electrode and the ring electrodes, a pair of puller wires 26 for bi-directional deflection of at least the intermediate section 14, and a pair of thermocouple wires 41, 45 to sense temperature at the distal section 15.

Figure 2C:
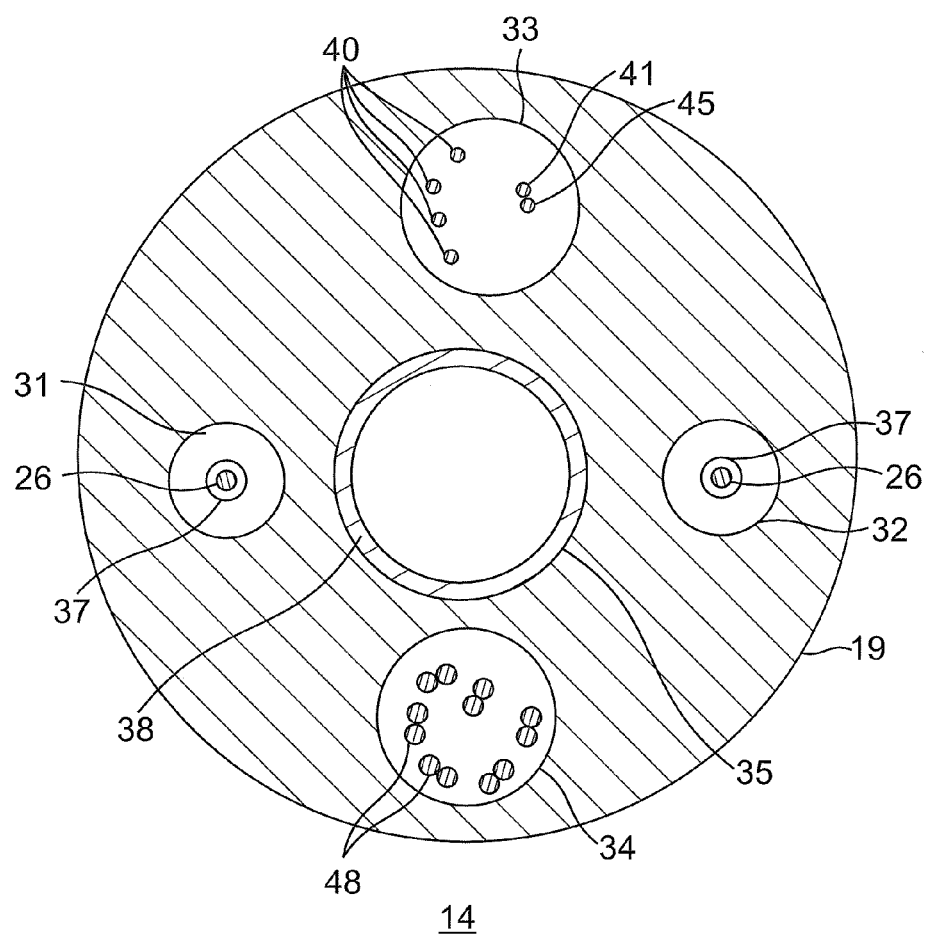
FIG. 2C is an end cross-section view of the deflectable intermediate section of FIG. 2B taken along line C-C.

Illustrated in FIGS. 2A, 2B and 2C is an embodiment of the intermediate section 14 which comprises a short section of tubing 19. The tubing also has a braided mesh construction with multiple off-axis lumens, for example five lumens 31, 32, 33, 34 and 35. Each of off-axis, diametrically opposing first and second lumens 31, 32 carries a puller wire 26. A third off-axis lumen 33 carries the lead wires 40 and the thermocouple wires 41 and 45. A fourth off-axis lumen 34 carries the sensor cables 48. A fifth on-axis lumen 35 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 24 that receives an inner surface of the outer wall 20 of the catheter body 12. The intermediate section 14 and catheter body 12 are attached by glue or the like.

If desired, a spacer (not shown) can be located within the catheter body 12 between the distal end of the stiffening tube 22 (if provided) and the proximal end of the intermediate section 14. The spacer provides a transition in flexibility at the junction of the catheter body 12 and intermediate section 14, which allows this junction to bend smoothly without folding or kinking. A catheter having such a spacer is described in U.S. Pat. No. 5,964,757, the disclosure of which is incorporated herein by reference.

Each puller wire 26 is preferably coated with Teflon® The puller wires 26 can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, a portion of each puller wire 26 extending through the catheter body 12 passes through a respective compression coil 37 in surrounding relation to its puller wire 26. The compression coil 37 extends from about the proximal end of the catheter body 12 to about the proximal end of the intermediate section 14. The compression coil 37 is made of any suitable metal, preferably stainless steel, and is tightly wound on itself to provide flexibility, i.e., bending, but to resist compression. The inner diameter of the compression coil is preferably slightly larger than the diameter of the puller wire 26. Within the catheter body 12, the outer surface of the compression coil 37 is also covered by a flexible, non-conductive sheath 39 (FIG. 2B), e.g., made of polyimide tubing. As shown in FIGS. 2B and 2C, a portion of each puller wire 26 extending through the intermediate section 14 is covered by a nonconductive protective sheath 47.

Proximal ends of the puller wires 26 are anchored in the control handle 16. Distal ends of the puller wires 26 may be anchored near the distal end of the intermediate deflectable section 14 or in the distal section 15 as desired or appropriate. Separate and independent longitudinal movement of the puller wires 26 relative to the catheter body 12 which results in deflection of the intermediate section 14 and/or tip section 15 is accomplished by suitable manipulation of the control handle 16.

In the illustrated embodiment of FIG. 1, the control handle 16 has a deflection actuator 50 that actuates the puller wires for bi-directional deflection. The control handle also includes a deflection tension knob 52 that enables the user to adjust the ease by which the deflection actuator 50 can be rotated. A suitable deflection assembly and control handle are described in co-pending U.S. application Ser. No. 12/346,834, filed Dec. 30, 2008, entitled DEFLECTABLE SHEATH INTRODUCER, the entire disclosure of which is hereby incorporated by reference. Other suitable deflection assemblies are described in co-pending U.S. application Ser. No. 12/211,728, filed Sep. 16, 2008, entitled CATHETER WITH ADJUSTABLE DEFLECTION SENSITIVITY, and U.S. application Ser. No. 12/127,704, filed May 27, 2008, entitled STEERING MECHANISM FOR BI-DIRECTIONAL CATHETER, the entire disclosures of both of which are hereby incorporated by reference.

Figure 3:
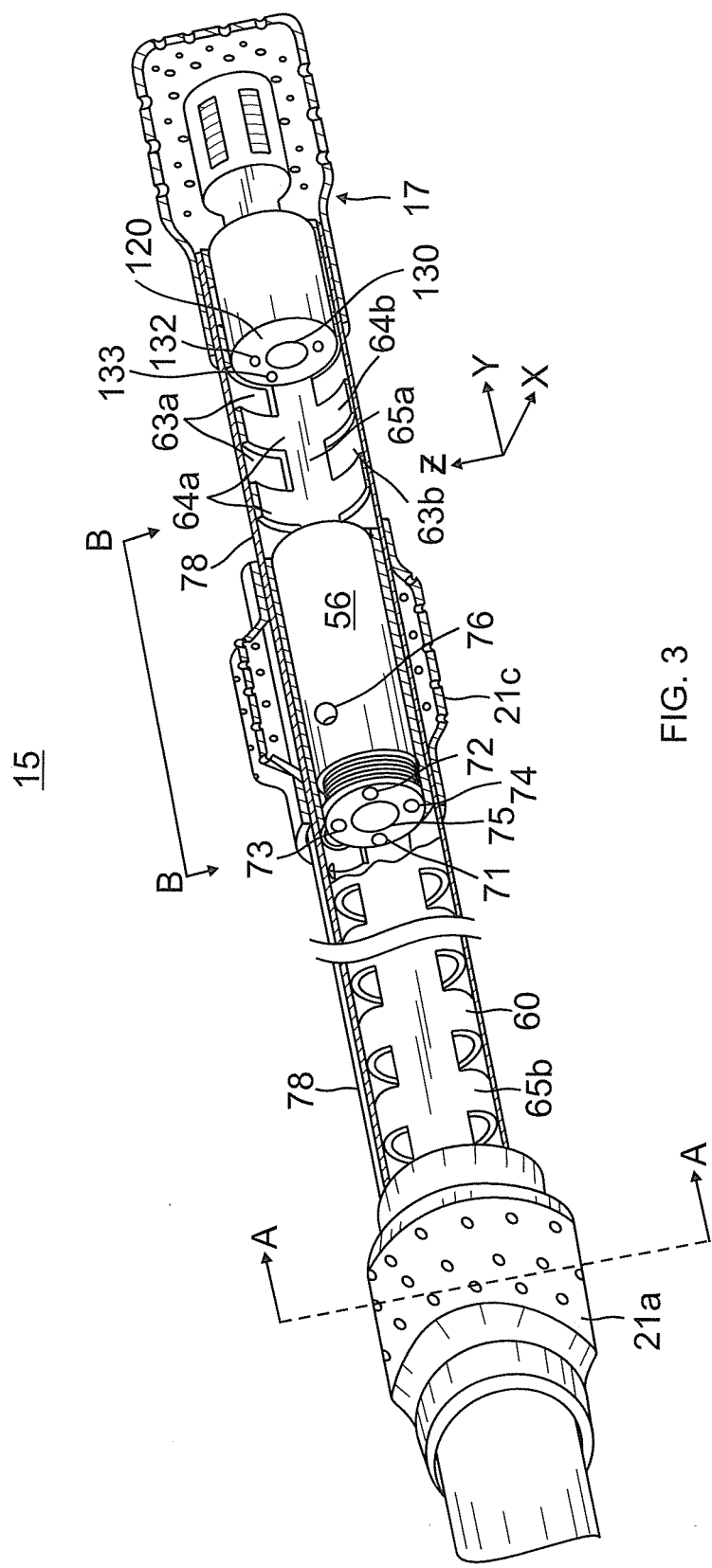
FIG. 3 is a perspective view of a distal section of the catheter of FIG. 1, with components broken away to show the interior.

With reference to FIG. 3, at the distal end of the intermediate section 14 is the distal section 15 that includes the tip electrode 17 and a plurality of irrigated ring electrodes 21 mounted at selected locations along the length of the distal section 15. Notwithstanding the ring electrodes 21, the distal section 15 advantageously has a flexible spring member 60 that allows for controlled or biased deflection in a single plane, in at least one direction, if not in two opposing directions, while allowing only limited deflection outside of the plane or in perpendicular directions to maintain torquability, axial loading capabilities, and side force performance. The spring member is constructed of a suitable material with flexibility and shape memory, such as nitinol or spring steel.

Figure 4A:
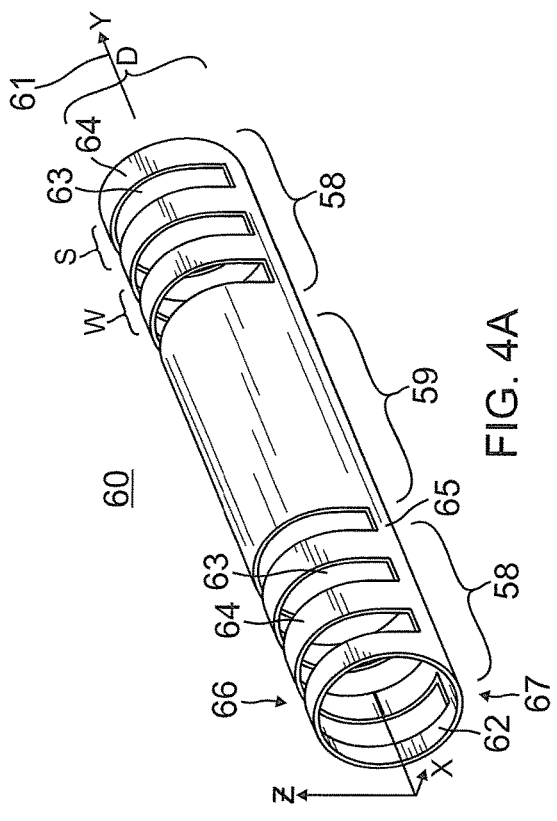
FIG. 4A is a perspective view of an embodiment of a spring member.

As illustrated in FIG. 4A, the spring member 60 has an elongated tubular form defining a longitudinal axis 61. The tubular form provides a central lumen 62 extending therethrough. In accordance with a feature of the present invention, the spring member 60 has a controlled or biased deflection that is enabled by at least one section 58 with defined compression characteristics enabled by a predetermined cut pattern, and at least one section 59 that is devoid of any cut pattern for carrying at least one ring electrode. The cut pattern of the section 58 includes a plurality of radial slots 63 with radial ribs 64 that extend from at least one spine 65 spanning the length of the tubular form. The slots 63 are cut or otherwise formed transversely, if not perpendicularly, to the longitudinal axis 61 of the tubular form, with each rib 64 having a generally uniform shape, depth D, width W and spacing S. These parameters may be varied as desired or appropriate for different deflection or bending characteristics. Illustrated herein are a few of the endless possible shapes of the slots, for example, trapezoidal (FIG. 5C), triangular (FIG. 5D), and circular or keyhole (FIG. 5E), and different depths, for example, less than half of the diameter of the tubular structure (FIG. 5C), about half of the diameter (FIG. 5D), or greater than half of the diameter (FIG. 5E). It is understood that tubular form itself may include tubes with circular or noncircular cross-sections.

The spring member 60 extends the length of the tip section 15 generally between a distal end of the intermediate deflectable section 14 and a proximal end of the tip electrode. The length may range between about 1.0 cm and 10.0 cm, preferably about 2.0 cm and 5.0 cm, and more preferably about 3.0 cm. In the illustrated embodiment, the spring member 60 has three pre-cut sections 58 and two uncut sections 59.

The distal section 15 as supported by the spring member 60 in its neutral configuration extends linearly (solid line in FIG. 1). The controlled or biased deflection (broken line in FIG. 1) is enabled by the spring member 60 having at least one side 66 along its length that is more elastically compressible as shown in FIG. 4A. The side 66 patterned by the slots 63 and ribs 64 is relatively more elastically compressible and the side 67 of the spine 65 is relatively less elastically compressible, if not resistant to compression. And, where the sides 66 and 67 are generally opposite to each other, as illustrated in FIG. 4A, the spring member 60 is biased to deflect within a single plane defined by the two sides 66 and 67 (namely, the YZ plane in FIG. 4A), and in one direction in the single plane (namely, toward the +Z axis).

Figure 4B:
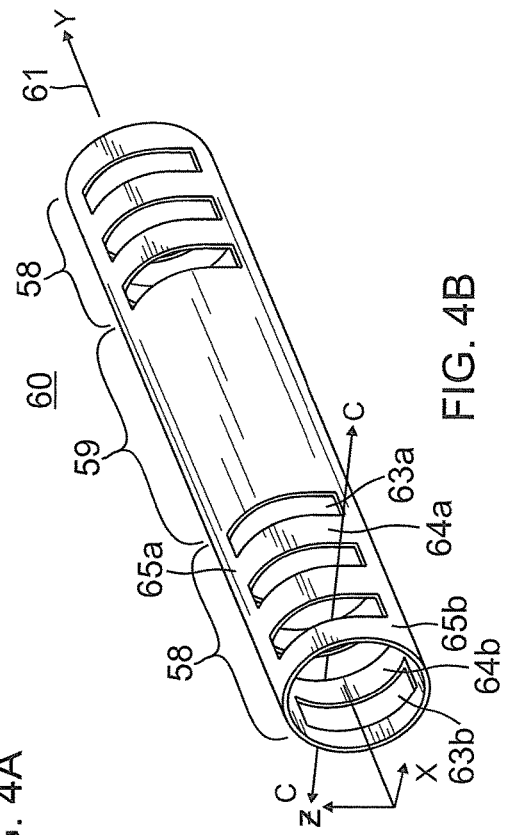
FIG. 4B is a perspective view of another embodiment of a spring member.
Figure 4C:
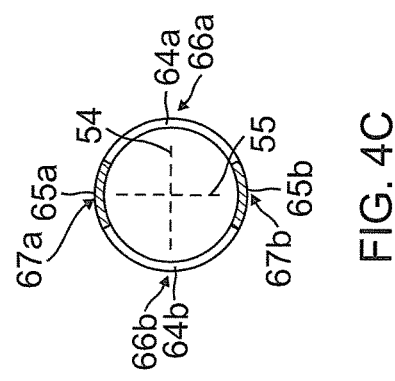
FIG. 4C is an end cross-sectional view of the spring member of FIG. 4B, taken along line C-C.

In an alternate embodiment, as illustrated in FIGS. 4B and 4C, the spring member 60 has two rows of radial slots 63a, 63b and ribs 64a, 64b, with each row extending along a respective side 66a, 66b that is relatively more elastically compressible, and two spines 65a, 65b with each spine extending along a respective side 67a, 67b that is relatively less elastically compressible, if not compression-resistant. And, where the two more compressible sides 66a, 66b are generally opposite of each other (separated by a radial angle of about 180 degrees) along a first diameter 54, the two less compressible sides 67a, 67b are generally opposite of each other (separated by a radial angle of about 180 degrees) along a second diameter 55 and the first and second diameters are generally perpendicular (separated by a radial angle of about 90 degrees), the spring member 60 is biased for deflection in a single plane (namely, the XY plane in FIG. 4B), and in opposite directions (or bi-directionally) within the single plane (namely, toward the +X axis and the −X axis). FIG. 4B illustrates the embodiment of the spring member 60 employed in the distal section 15 in FIG. 3.

Figure 5A:
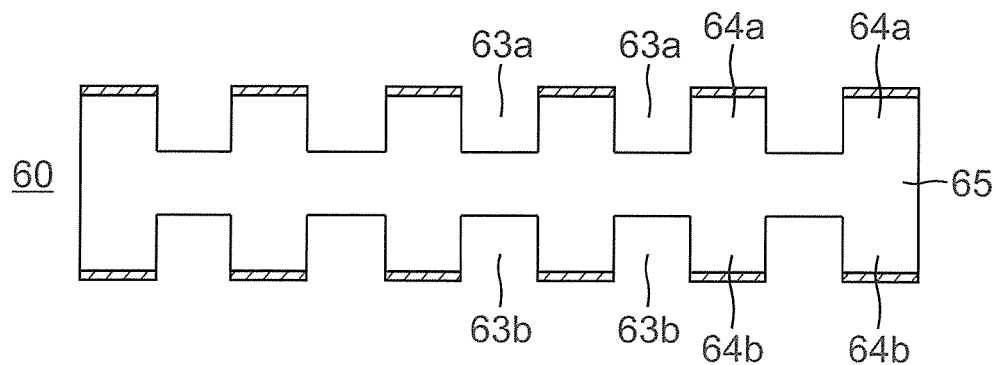
FIG. 5A is a side sectional view of an embodiment of a spring member.
Figure 5B:
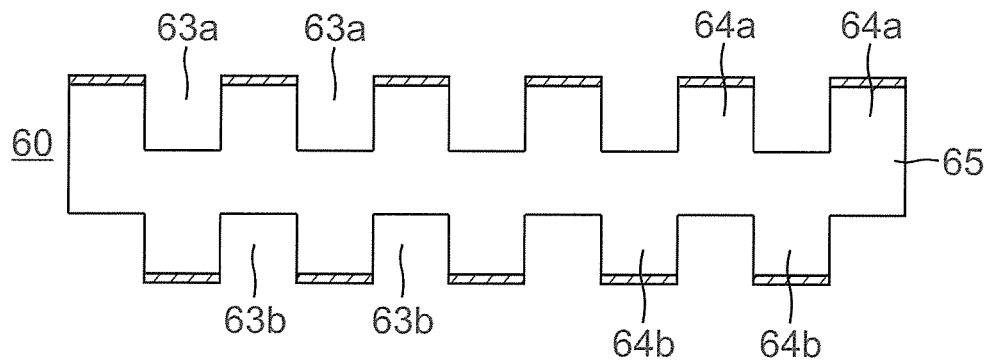
FIG. 5B is a side sectional view of another embodiment of a spring member.
Figure 5C:
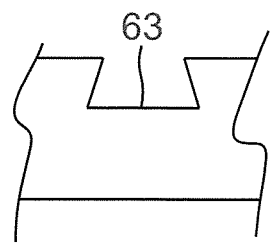
FIG. 5C is a detailed side view of an embodiment of a slot of a spring member.
Figure 5D:
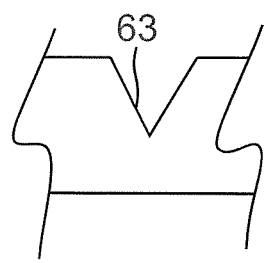
FIG. 5D is a detailed side view of another embodiment of a slot of a spring member.
Figure 5E:
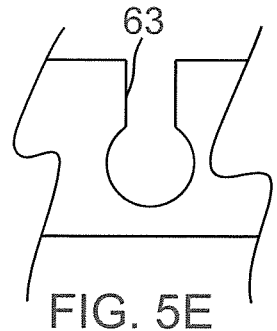
FIG. 5E is a detailed side view of yet another embodiment of a slot of a spring member.

In FIGS. 4A and 4B, the slots 63a and ribs 64a are aligned respectively with the slots 63b and ribs 64b, as better shown in FIG. 5A. However, it is understood that the slots and ribs of different rows can be offset from each other such that they present an alternating pattern, as shown in FIG. 5B.

It is understood by one of ordinary skill in the art that deflection characteristics of a spring member depends on various factors, including plurality, depth D, separation S, width W of any row of slots/ribs, especially where a spring member has more than one row of slots/ribs with different pluralities, depths and/or widths such that the spines have different widths and/or are not opposite of each other such that their radial separation angle is greater or less than about 180 degrees.

The integrity of the spring member 60 is maintained by including a flexible cover 78 over the spring member, as shown in FIG. 3. The cover is preferably made of a biocompatible plastic or polymer, such as PELLETHANE or PEBAX, or polyolefin, with a flexibility about equal to that of the spring member. The cover should not hinder the ability of the spring member to bend. The cover protects the spring member against electrical conductivity, particularly where the structure is made of Nitinol or another metal, and also protects against blood and other bodily fluids from entering and clogging the slots. The cover 78 can be longer than the member 60 and has proximal and distal ends extending beyond the member's proximal and distal ends, respectively. The cover can be secured in place over the member by any suitable methods, such as by gluing, thermal bonding and/or heat shrinking.

Figure 3A:
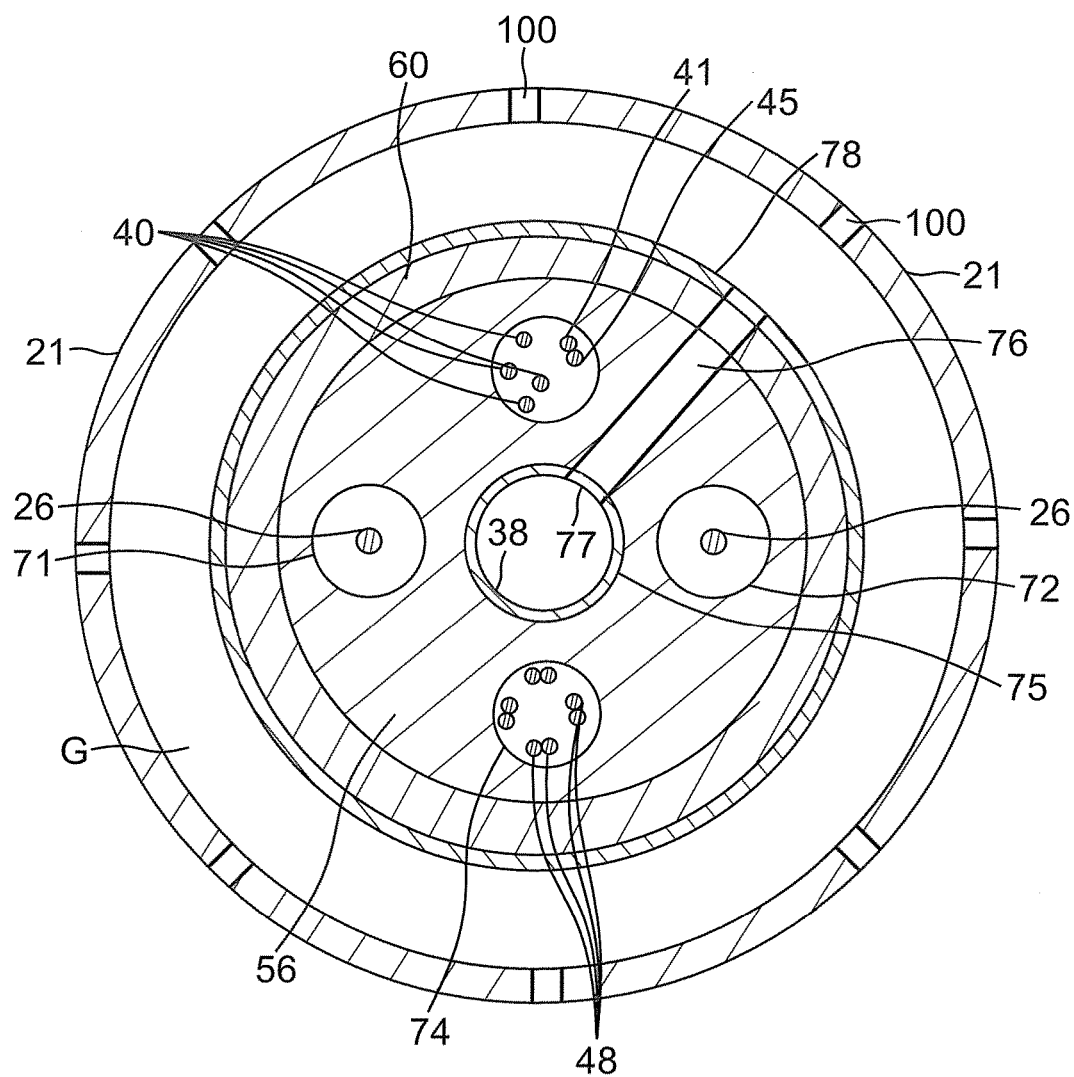
FIG. 3A is an end cross-sectional view of the distal section of FIG. 3, taken along line A-A.
Figure 3B:
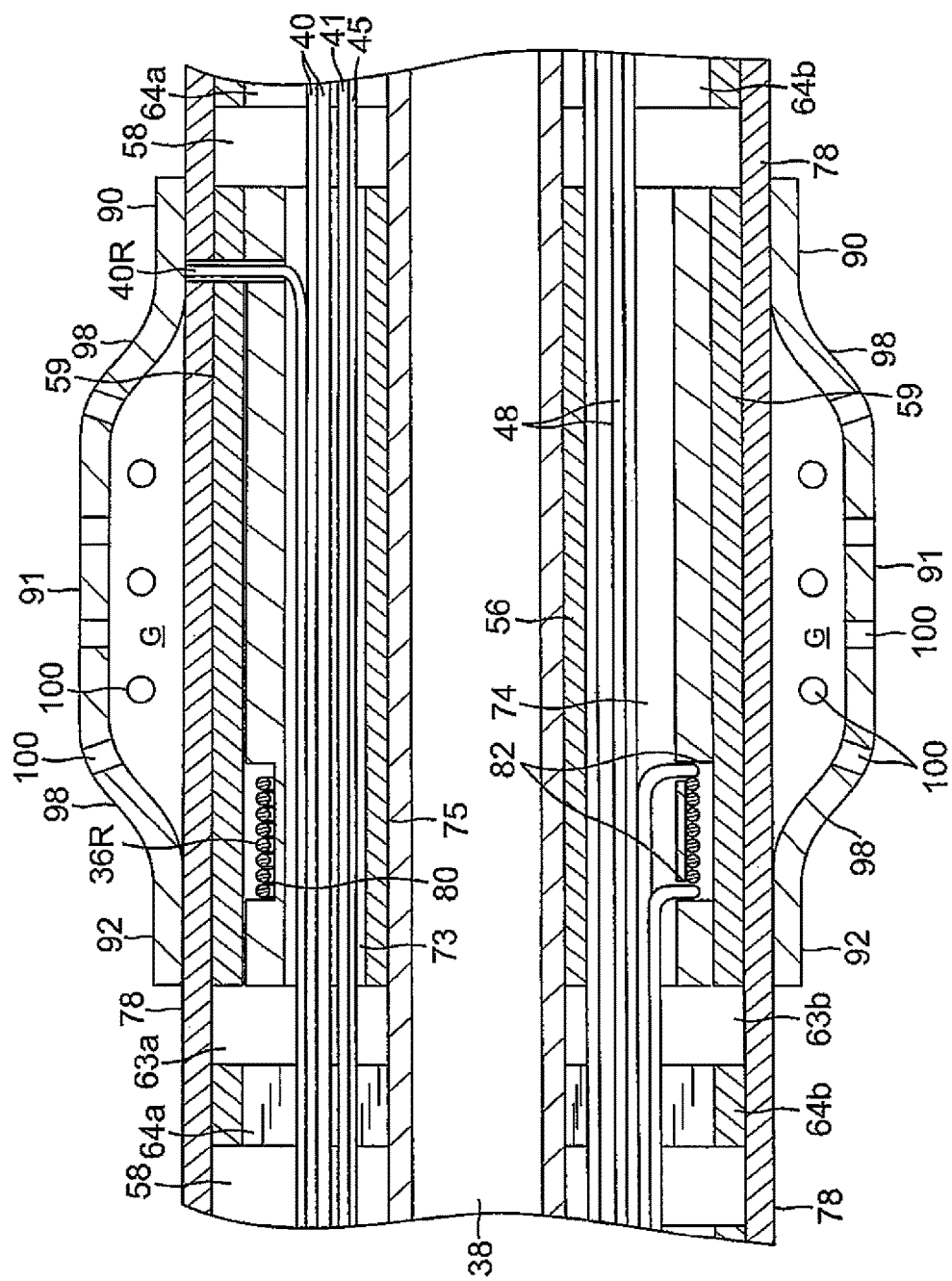
FIG. 3B is a side cross-sectional view of the distal section of FIG. 3, taken along line B-B.

At least one ring electrode 21 is carried on the spring member 60 over the cover 78. In the illustrated embodiment, there are three ring electrodes 21a, 21b, 21c, although it is understood that the plurality can range between about 2 and 10, and preferably between about 3 and 5. At each ring electrode 21, a support member 56 is positioned in the central lumen 62 of the spring member 60 to support its respective ring electrode. The support member 56 may be constructed of a sufficiently rigid plastic material suitable for housing position/location sensors, such as SASs, to regulate irrigation flow to irrigated ring electrodes 21 and to act as a substrate on which its respective ring electrode is mounted. With reference to FIGS. 3, 3A and 3B, each support member 56 has a similar construction with a plurality of lumens, including at least lumens 73, 74, 75 that preferably are in axial alignment with the lumens 33, 34 and 35, respectively, of the tubing 19 of the deflectable intermediate section 14, to avoid sharp bends or kinks in the components extending through these lumens. In the illustrated embodiment of FIG. 3A, each member 56 includes an off-axis lumen 73 for electrode lead wires 40 and thermocouple wires 41, 45, an off-axis lumen 74 for sensor cables 48, and a center lumen 75 for irrigation fluid. The member may also include off-axis, diametrically opposing lumens 71 and 72 for the puller wires 26 in an embodiment where the puller wires extend into the distal section 15.

The length of each support member 56 can range between about 0.2 cm and 1.0 cm, and preferably about 0.5 cm, which is generally about equal to the length of a ring electrode. The support members 56 may be fabricated using micro machining, micro molding, or machining of extrusions using plastic materials which are sufficiently rigid and sufficiently biocompatible for contact with blood.

A circumferential groove 80 is formed in the outer surface of each support member 56. In the illustrated embodiment of FIGS. 3 and 3B, the groove 80 is formed near a proximal end of the support member 56, although it is understood that the groove 80 may be formed near a distal end of the support member 56. The groove 80 is provided on the support member 56 to carry a wire coil of a sensor 36R for each irrigated ring electrode 21. The wire coil (e.g., a single-axis sensor "SAS") is advantageously wound in the groove 80 on the support member 56 so that it does not occupy any space in the distal section 15 beyond that already occupied by the support member 56. Moreover, the wire coil does not occupy any lumens of the support member 56. Rather, the lumens are available to other components, including lead wires, thermocouple wires, irrigation tubing and puller wires, that do not necessarily require dedicated lumens and/or larger lumens as a typical sensor would.

A pair of sensor cables 48 are provided for each coil sensor 36R of a ring electrode 21, with each end of the coil being connected to one of the pair of cables (FIG. 3B). The sensor cables 48 for each coil of the ring electrodes 21 (and for the position sensor 36T in the tip electrode 17) extend through the fourth lumen 74 of the support member 56. A passage 82 (FIG. 3B) through the support member 56 allowing communication between the lumen 74 and the groove 80 is provided at each end of the groove. One sensor cable 48 is fed through a respective passage 82 for connection to each end of the wire coil of the sensor 36R, so each sensor 36R has a pair of sensor cables connected to it.

Figure 6:
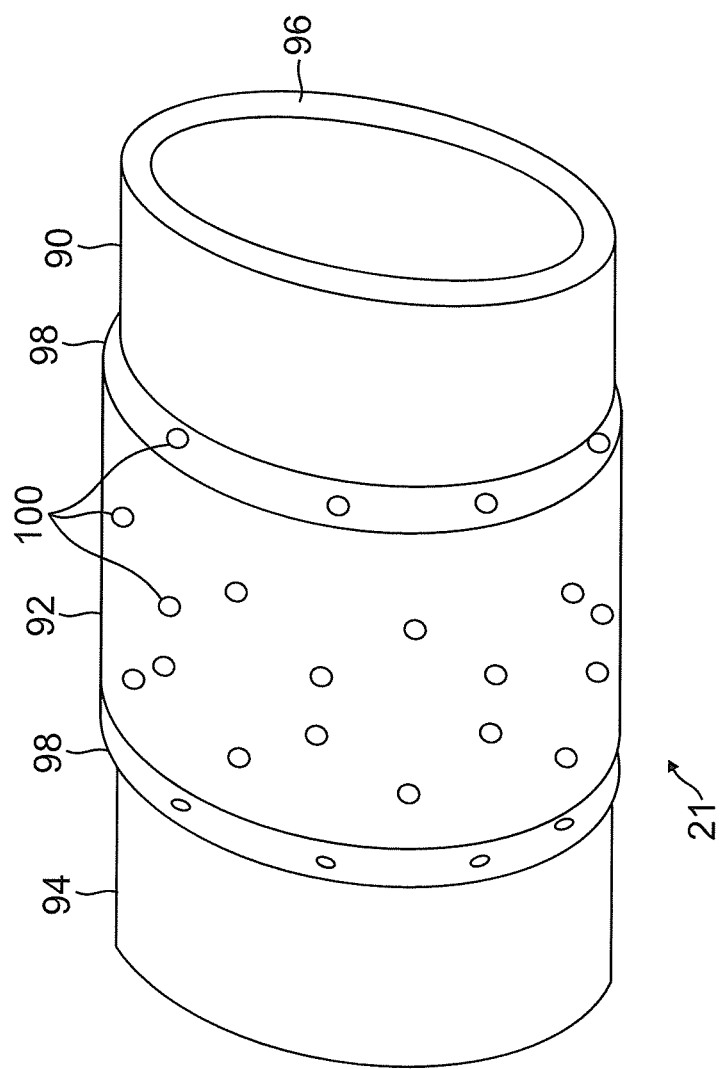
FIG. 6 is a perspective view of an embodiment of a ring electrode.

Each of the irrigated ring electrodes 21 is adapted for ablation and irrigation and has a similar structure to each other. The ring electrodes may be made of any suitable noble metal, such as platinum or gold, preferably a combination of platinum and iridium or gold and platinum. In the illustrated embodiment of FIG. 6, the ring electrode 21 is generally cylindrical with a length greater than its diameter and has a distal end 90, a mid-section 92 and a proximal end 94. With a wall 96 of a generally uniform thickness throughout its length, the ring electrode 21 has a larger diameter in the mid-section 92 than in the distal and proximal ends 90, 94. As such, the wall bulges outwardly in the mid-section with curved transitional regions 98 on each side of the mid-section 92 so as to provide the ring electrode with an atraumatic profile without corners or sharp edges. With reference to FIGS. 3A and 3B, a reservoir in the shape of an annular gap G is formed between an inner surface of the mid-section 92 and an outer surface of the spring member 60 (inclusive of the cover 78). A plurality of irrigation apertures 100 are formed in the wall 96 of the mid-section 92 to promote flow in a radial direction, and of the curved transitional regions 98 to promote flow in a more axial direction. In the latter instance, the apertures 100 in the curved transitional regions 98 are particularly effective in minimizing charring and coagulation which are likely to be "hot spots" resulting from higher current densities due to transitions in the electrode profile. In that regard, the curved transitional regions 98 may have a higher aperture density and/or apertures with a greater cross-section so as to minimize the occurrence of hot spots. Suitable ring electrodes are described in US Patent Application Publication No. US2010/0168548 A1, and U.S. patent application Ser. No. 13/174,742, filed Jun. 30, 2011, the entire content of both of which are incorporated herein by reference.

The ring electrodes 21 can be made of any suitable solid conductive material, such as platinum or gold, preferably a combination of platinum and iridium. The ring electrodes can be mounted onto the support members 56 with glue or the like. The rings electrodes may be uni-polar or bi-polar. In the illustrated embodiment, there are a distal monopolar ring electrode and a proximal pair of bi-polar ring electrodes. Each ring electrode is connected to a respective lead wire 40R.

Each lead wire 40R is attached to its corresponding ring electrode 21 by any suitable method. A preferred method for attaching a lead wire to a ring electrode involves first making a small hole through the wall of the non-conductive covering or tubing. Such a hole can be created, for example, by inserting a needle through the support member 56 and its cover 78 and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like.

As seen in FIGS. 3 and 3A, at least one opening 77 is formed in each portion of the irrigation tubing 38 extending through each ring electrode 21. The opening 77 communicates with a radial passage 76 formed in the spring member 60, its cover 78, and the support member 56 below each ring electrode 21. The passage 76 extends radially from the lumen 75 of the support member 56, through the support member 56, the spring member 60 and the cover 78 to provide fluid communication between the irrigation tubing 38 and the gap reservoir G of each ring electrode 21. Each passage 76 is formed at a predetermined radial angle (FIG. 3A) so that the passages 76 do not intersect or otherwise interfere with the off-axis lumens in each of the support member 56. Advantageously, the passages 76 can be precisely dimensioned so as to regulate the volumetric flow rate of the irrigation fluid delivered to the gap reservoirs G.

The length of a ring electrode 21 is about equal to the length of a support member 56 so that the support member is covered in its entirety by its respective ring electrode. The groove 80 and the coil sensor 36R are positioned under a section 59 of the spring member so that the coil sensor 36R is isolated from and not exposed to irrigation fluid in the gap reservoir G of the ring electrode. The distal and proximal ends 90 and 94 of the ring electrodes are sized relative to the support members 56 so as to form a fluid tight seal enclosing the gap reservoir G.

Figure 7:
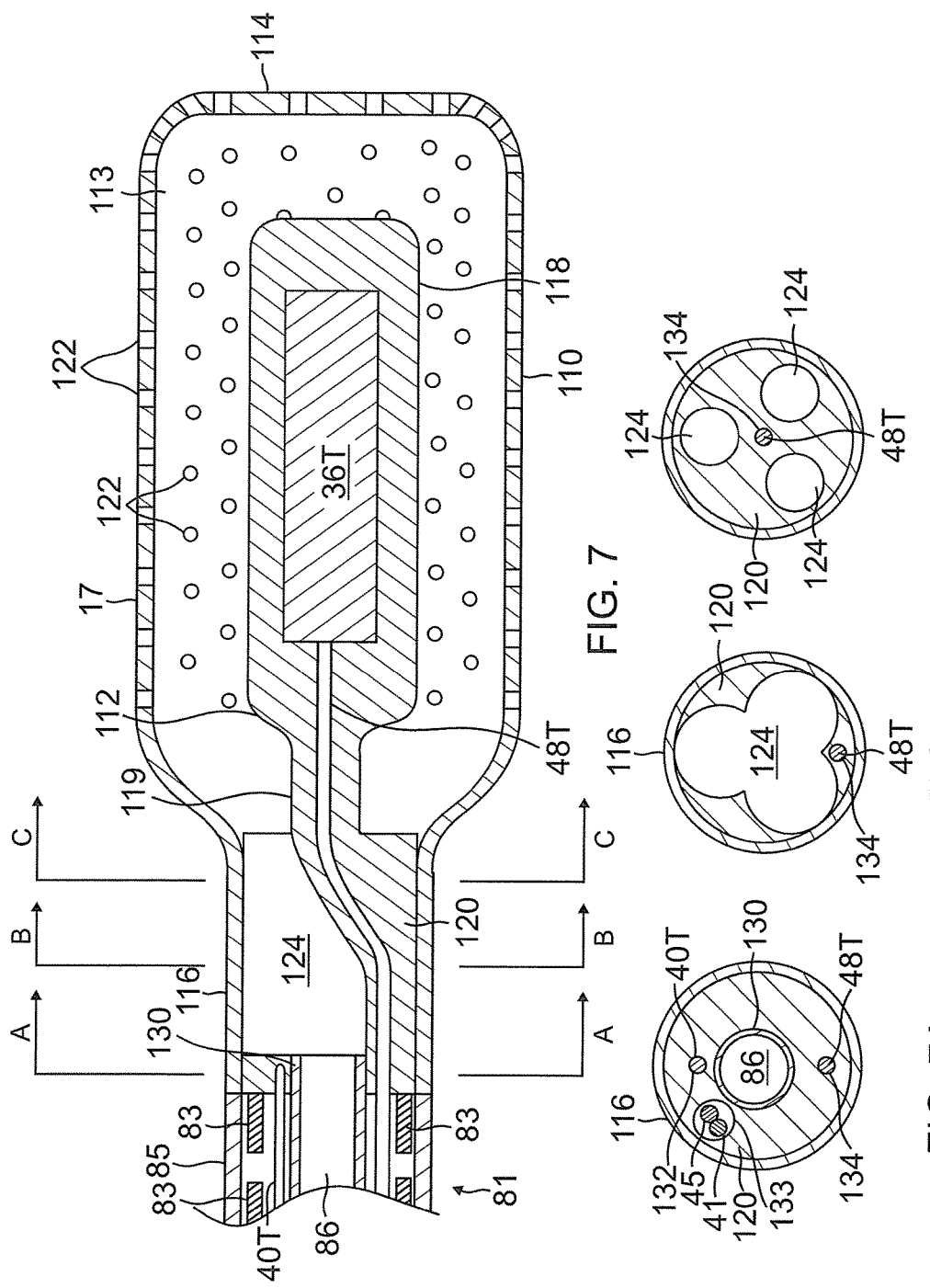
FIG. 7 is a side cross-sectional view of the tip electrode of FIG. 3.

With reference to FIGS. 3 and 7, the tip electrode 17 houses an electromagnetic position sensor 36T in a distal and on-axis location relative to the tip electrode. The tip electrode is configured to promote turbulent flow and dispersion of irrigation fluid for increased thermal transfer from the tip electrode to the fluid and thus with lower flow rates resulting in lower fluid load in the patient. Fluid, e.g., saline or heparinized saline, can be delivered to the ablation site from the tip electrode to cool tissue, reduce coagulation and/or facilitate the formation of deeper lesions. It is understood that other fluids can be delivered as well, including any diagnostic and therapeutic fluids, such as neuroinhibitors and neuroexcitors.

The tip electrode 17 has a two-piece configuration that includes an electrically conductive dome shell 110 and an internal member 112. The shell 110 is generally cylindrical defining a chamber 113 between a closed distal end 114 and an open proximal end (or neck) 116. The neck 116 connected with a distal end of the nonconductive cover 85 of the connection section 81. The internal member 112 is configured to fit inside the shell 110 with an elongated distal section 118 that sits inside the chamber 113, and a proximal core 120 that plugs the neck 116. The core 120 and the distal section 118 are connected by a stem 119. The distal end 114 of the shell 110 and the distal section 118 of the internal member 112 are relatively sized so that the chamber 113 functions as a tip reservoir for irrigation fluid entering the tip electrode 17. Fluid passages 124 are formed in the core 120 to provide fluid communication from the irrigation connector lumen 86 to the chamber 113.

The shell 110 is constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell is constructed of an alloy comprising about 90% platinum and about 10% iridium by weight. The shell can formed by deep-drawing manufacturing process which produces a sufficiently thin but sturdy wall that is suitable for handling, transport through the patient's body, and tissue contact during mapping and ablation procedures. A deep drawn shell is also suitable for electrical discharge machining (EDM) process to form a large plurality of through-holes or ports 122 in the shell that allow fluid communication between the chamber 113 and outside the shell 110.

The elongated distal section 118 of the internal member 112 is configured to protect and encapsulate the tip electrode sensor 36T which is positioned centrally within the chamber 113 so that the sensor is distal and centered in the tip electrode for optimum performance. In the disclosed embodiment, the tip electrode sensor 36T is an electromagnetic (EM) tri-axis location/position sensor using three coils that give rise to signals that are used to determine the position of the device relative to a frame of reference that is fixed either externally to the body or to the heart itself. The EM sensor may be active or passive and may operate by generating or receiving electrical, magnetic or ultrasonic energy fields or other suitable forms of energy known in the art.

The core 120 of the internal member 112 sits in the neck 116 of the shell 110. The core is advantageously configured as a diffuser that provides multiple fluid passages or channels 124 through the neck 116 so as to diffuse the irrigation fluid. As such, the diffusing core 120 provides increased turbulence and a more uniform flow rate in the chamber 113 and thus more increased convective cooling on the shell 110. Irrigation in the tip electrode 17 is thus more uniform throughout the length of the tip electrode. The internal member 112 effectively counters the tendency for the velocity of the fluid entering the tip electrode 17 to otherwise carry the fluid to the more distal ports and starve the more proximal ports 122.

On a proximal surface of the core 120, a center opening 130 (FIG. 7A) connects a distal end of the irrigation tubing 38 with the channels 124 in the core 120. Within the core 120, the channels 124 intersect each other at varying degrees throughout the tip electrode (FIG. 7B), and then separate into distinct channels (FIG. 7C.) In the illustrated embodiment, the channels 124 have a circular cross-section, however, it is understood that the cross-section may be polygonal or any noncircular shape and can have any suitable size, as appropriate. The core 120 is made of electrically conductive material so as to be conductive with the shell 110 when the core 120 is energized by its lead wire 40T, but the distal section 118 can be made of plastic such as polyimide, or an adhesive or sealant, such as epoxy, to encapsulate the tip electrode sensor 36T.

Also on the proximal surface of the core 120 are blind holes 132, 133 (FIGS. 3 and 7 A) for the tip electrode lead wire 40T, the thermocouple wires 41, 45. A longitudinal through-hole 134 extending through the core 120, the stem 119 and into the distal section 118 of the internal member 112 is provided for the cable 48T for the tip electrode sensor 36T. The through-hole or passage 134 is routed from a proximal off-axis location in the core 120 to a distal on-axis location in the stem 119 without interfering with the fluid diffusing channels 124.

Figure 8:
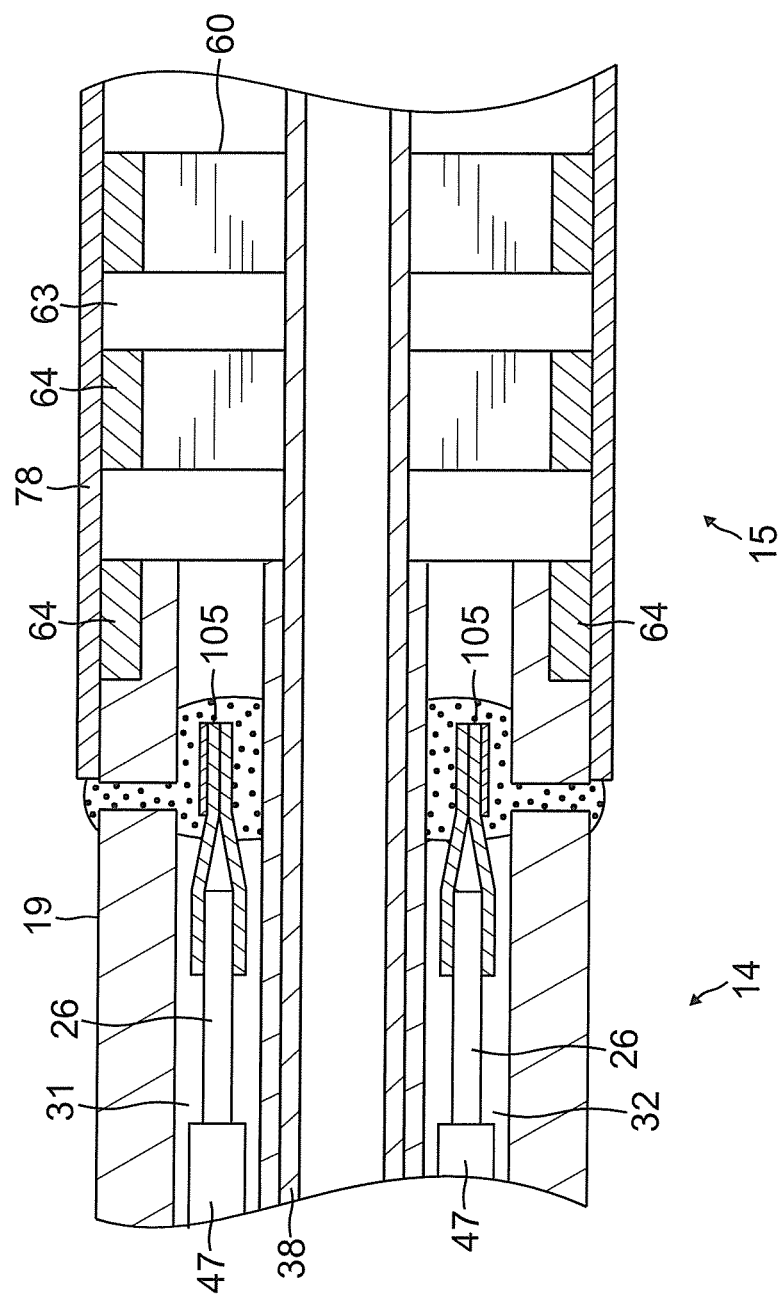
FIG. 8 is a side cross-sectional view of the catheter of FIG. 1, showing a junction between an intermediate section and a distal section, taken along a diameter.

A distal end of each puller wire 26 has a T-bar 105. In the illustrated embodiment of FIG. 8, the T-bars are anchored in the first and second lumens 31, 32 of the tubing 19 at or near the distal end of the intermediate section 14. However, it is understood that the distal ends of the puller wires 26 may be soldered in diametrically-opposing off axis blind-holes in the proximal surface of the core 120 (FIG. 3) of the tip electrode 17, as desired or appropriate.

In accordance with another feature of the present invention, fluid is delivered through the catheter body 12 (FIG. 2A), through the intermediate section 14 (FIG. 2A), and through the distal section 15 via the irrigating tubing 38 (FIG. 3B) which extends through the lumen 75 of the support members 56. A portion of the fluid enters the reservoir gap G of each ring electrode via the opening 77 and the passage 76 (FIG. 3C), and exits the ring electrodes via the apertures 100. Another portion of the fluid continues to the tip electrode 17 via the irrigation tubing 38 and the diffusing channels 124 (FIG. 5), where it enters the chamber 113 and exits the tip electrode via irrigation ports 122. In the tip electrode 17, the fluid has a flow that is more uniform and equal in the radial direction through the diffusing channels 124 which in turn provides increased turbulence and a more uniform flow rate in the chamber 113 and thus more increased convective cooling on the shell 110. Irrigation in the tip electrode is thus more uniform throughout the length of the tip electrode. Suitable tip electrodes are described in U.S. patent application Ser. No. 12/767,763, filed Apr. 26, 2010 entitled "IRRIGATED CATHETER WITH INTERNAL POSITION LOCATION SENSOR," the entire disclosure of which is incorporated herein by reference.

The lead wires 40T and 40R pass through the lumen 18 of the catheter body 12 (FIG. 2A), the lumen 33 of the intermediate section 14 (FIG. 2A), and the lumen 73 of the support members 56 (FIG. 3B) throughout the distal section 15. The portion of the lead wires extending through the central lumen 18 of the catheter body 12, and proximal portion of the lumen 33 can be enclosed within a protective sheath 67 (FIG. 2A), which can be made of any suitable material, preferably polyimide. The protective sheath is anchored at its distal end to the proximal end of the intermediate section 14 by gluing it in the lumen 33 with polyurethane glue or the like. Each electrode lead wire has its proximal end terminating in a connector (not shown) at the proximal end of the control handle 16. The tip electrode 17 and ring electrodes 21 are electrically connected to a source of ablation energy by the lead wires 40T and 40R via the connector. The wires may also be electrically connected to an appropriate mapping or monitoring system via the connector.

The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Certain features, including the cut pattern of slots, ribs and spine, may be exaggerated for clarity purposes. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. A catheter adapted to carry a position sensor, comprising:
   an elongated catheter body;
   a distal section distal the elongated catheter body, the distal section comprising:
      a spring member having a length defining a longitudinal axis and a central lumen extending along the length, the spring member having a monolithic construction including at least two first sections and at least two second sections, the at least two first sections alternating in longitudinal location with the at least two second sections, each of the at least two second sections having at least one spine extending longitudinally along a first side of the spring member and at least one rib defined by a plurality of slots along a second side of the spring member, the at least one rib and the plurality of slots being transverse to the longitudinal axis, and each of the at least two first sections being devoid of the plurality of slots;
      a ring electrode carried on each of the at least two first sections of the spring member, each of the at least two first sections of the spring member having a length sufficient to carry its respective ring electrode;
      at least one support member positioned in the central lumen in each of the at least two first sections of the spring member to support the respective ring electrode; and
      a tip electrode;
   wherein the spring member is compressible in the at least two second sections along the second side generally opposite the first side in providing a biased deflection of the distal section in a single plane.

2. The catheter of claim 1, wherein the biased deflection of the distal section is in a single plane and in a single direction.

3. The catheter of claim 1, wherein the spring member has a nonconductive coating.

4. The catheter of claim 1, further comprising a fluid-tight sheath extending over the spring member.

5. The catheter of claim 1, wherein an irrigation fluid path is provided through the at least one support member to deliver irrigation fluid to at least one of the ring electrodes.

6. The catheter of claim 1, wherein the at least one support member carries a coil sensor that is wound around an outer surface of the at least one support member.

7. The catheter of claim 6, wherein the coil sensor is wound in a groove formed in an outer surface of the at least one support member.

8. The catheter of claim 6, wherein the coil sensor sits in a groove formed on an outer surface of the at least one support member.

9. The catheter of claim 6, wherein the coil sensor is located between the respective ring electrode and the at least one support member.

10. The catheter of claim 1, wherein the respective ring electrode is configured to form a gap reservoir between an outer surface of the spring member and an inner surface of the respective ring electrode.

11. The catheter of claim 10, further comprising an irrigation fluid path through the elongated catheter body and into the distal section through the central lumen of the spring member and reaching the respective ring electrode, wherein an irrigation passage is formed in the at least one support member and the respective ring electrode to provide fluid communication between the irrigation fluid path and the gap reservoir.

12. The catheter of claim 1, wherein the at least one support member has at least one from the group consisting of a lead wire lumen, a sensor cable lumen and an irrigation lumen.

13. The catheter of claim 1, wherein the tip electrode includes:
   a shell defining a chamber, the shell having fluid ports;
   an internal member carrying a tip location sensor, the internal member having a diffuser to diffuse fluid entering the chamber.

* * * * *